(12) United States Patent
Agre et al.

(10) Patent No.: US 11,304,880 B2
(45) Date of Patent: Apr. 19, 2022

(54) GLASS IONOMER COMPOSITIONS AND METHODS INCLUDING WATER-MISCIBLE, SILANE-TREATED, NANO-SIZED SILICA PARTICLES

(71) Applicant: 3M INNOVATIVE PROPERTIES COMPANY, St. Paul, MN (US)

(72) Inventors: Mark B. Agre, Rochester, MN (US); Bradley D. Craig, Lake Elmo, MN (US); Michael Jahns, Gilching (DE); Adrian S. Eckert, Herrsching (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 338 days.

(21) Appl. No.: 16/613,368

(22) PCT Filed: May 9, 2018

(86) PCT No.: PCT/US2018/031771
§ 371 (c)(1),
(2) Date: Nov. 13, 2019

(87) PCT Pub. No.: WO2018/213074
PCT Pub. Date: Nov. 22, 2018

(65) Prior Publication Data
US 2020/0069535 A1 Mar. 5, 2020

Related U.S. Application Data

(60) Provisional application No. 62/507,874, filed on May 18, 2017.

(51) Int. Cl.
*A61K 6/889* (2020.01)
*C03C 3/062* (2006.01)
*C03C 4/00* (2006.01)

(52) U.S. Cl.
CPC .............. *A61K 6/889* (2020.01); *C03C 3/062* (2013.01); *C03C 4/0021* (2013.01)

(58) Field of Classification Search
CPC ........ A61K 6/889; C03C 3/062; C03C 4/0021
See application file for complete search history.

(56) References Cited

U.S. PATENT DOCUMENTS

| | | |
|---|---|---|
| 4,209,434 A | 6/1980 | Wilson |
| 4,360,605 A | 11/1982 | Schmitt |
| 4,376,835 A | 3/1983 | Schmitt |
| 4,569,954 A | 2/1986 | Wilson |
| 5,250,585 A | 10/1993 | Guggenberger |
| 5,332,429 A | 7/1994 | Mitra |
| 5,918,772 A | 7/1999 | Keller |
| 5,944,419 A | 8/1999 | Streiff |
| 6,899,948 B2 | 5/2005 | Zhang |
| 7,090,721 B2 | 8/2006 | Craig |
| 7,156,911 B2 | 1/2007 | Kangas |
| 7,649,029 B2 | 1/2010 | Kolb |
| 10,548,818 B2 * | 2/2020 | Jahns ............... A61K 6/75 |
| 2004/0010055 A1 | 1/2004 | Bui |
| 2005/0252413 A1 | 11/2005 | Kangas |
| 2005/0256223 A1 | 11/2005 | Kolb |
| 2006/0187752 A1 | 8/2006 | Keller |
| 2007/0090079 A1 | 4/2007 | Kelller |

FOREIGN PATENT DOCUMENTS

| | | |
|---|---|---|
| EP | 0368657 | 5/1990 |
| WO | WO 2001-030307 | 5/2001 |
| WO | WO 2005-016783 | 2/2005 |
| WO | WO 2007-104037 | 9/2007 |
| WO | WO 2009-061884 | 5/2009 |
| WO | WO 2010-123800 | 10/2010 |
| WO | WO 2015-088956 | 6/2015 |
| WO | WO 2017-015193 | 1/2017 |

OTHER PUBLICATIONS

International Search report for PCT International Application No. PCT/US2018/031771 dated Aug. 6, 2018, 5 pages.

* cited by examiner

*Primary Examiner* — C Melissa Koslow

(74) *Attorney, Agent, or Firm* — 3M Innovative Properties Company

(57) ABSTRACT

Disclosed herein are curable glass ionomer compositions that include a first paste and a second paste, and methods for using the disclosed compositions. The first paste includes water, a polyacid, and a non acid-reactive filler. The second paste includes water, an acid-reactive filler; and non-aggregated, water-miscible, nano-sized silica particles having at least 25% surface coverage of the particles with a silane. The composition is essentially free of a resin. In some embodiments, the water content of the first paste and the second paste of the paste/paste GI composition disclosed herein is less than 20% by weight, based on the total weight of the composition.

20 Claims, No Drawings

GLASS IONOMER COMPOSITIONS AND METHODS INCLUDING WATER-MISCIBLE, SILANE-TREATED, NANO-SIZED SILICA PARTICLES

CROSS REFERENCE TO RELATED APPLICATIONS

This application is a national stage filing under 35 U.S.C. 371 of PCT/US2018/031771, filed May 9, 2018, which claims the benefit of U.S. Provisional Application No. 62/507,874, filed May 18, 2017, the disclosures of each of which are incorporated by reference herein in their entireties.

BACKGROUND

Conventional Glass Ionomer (GI) compositions are dental materials composed of an acid-reactive filler such as a fluoroaluminosilicate (FAS) glass, a polyacid such as a water-soluble polymer with carboxylic groups, and water. Acid groups in the polyacid can react with the metal cations from the acid-reactive filler in a "setting" reaction to form a matrix. When FAS glass is used as an acid-reactive filler, fluoride ions are released as a byproduct. Many conventional GI compositions also incorporate a complexing agent such as tartaric acid to retard the setting reaction. Although selecting specific acid-reactive fillers (e.g., compositions and/or particle size distributions), selecting specific polyacids (e.g., compositions based on acrylic, maleic, and/or itaconic acids and acidic group content), and selecting the loading level of the acid reactive filler in the GI composition can modify the reactivity of a GI composition, the selection of components has not resulted in major improvements in ease of mixing the components and strength and aesthetics of the cured composition.

Both composites and conventional GI compositions can be used as restorative materials. However, compared to composites, GI compositions can offer advantages such as fluoride release, diminished sensitivity, and self-adherence to a tooth. However, compared to composites, low mechanical properties and less desirable aesthetics have limited the use of GI compositions for many applications. Further, conventional powder/liquid GI compositions can be difficult to mix.

There is a continuing need for improved GI dental materials.

SUMMARY

In one aspect, the present disclosure provides curable glass ionomer compositions that include a first paste and a second paste. In one embodiment, the curable glass ionomer composition includes: a first paste including water, a polyacid, and a non acid-reactive filler; and a second paste including water, an acid-reactive filler; and non-aggregated, water-miscible, nano-sized silica particles having at least 25% surface coverage of the particles with a silane; wherein the composition is essentially free of a resin.

In another aspect, the present disclosure provides a device for storing a curable glass ionomer composition as described herein that includes a first paste including water, a polyacid, and a non acid-reactive filler; and a second paste including water, an acid-reactive filler; and non-aggregated, water-miscible, nano-sized silica particles having at least 25% surface coverage of the particles with a silane; wherein the composition is essentially free of a resin. The device includes: a first compartment containing the first paste; and a second compartment containing the second paste. In some embodiments, both the first compartment and the second compartment each independently includes a nozzle or an interface for receiving an entrance orifice of a static mixing tip.

In another aspect, the present disclosure provides a method of preparing a cured composition.

In one embodiment, the method includes providing a curable glass ionomer composition as described herein that includes a first paste including water, a polyacid, and a non acid-reactive filler; and a second paste including water, an acid-reactive filler; and non-aggregated, water-miscible, nano-sized silica particles having at least 25% surface coverage of the particles with a silane; wherein the composition is essentially free of a resin; combining the first paste and the second paste to form a mixture; and allowing the mixture to cure to form the cured composition.

In another embodiment, the method includes providing a device for storing a curable glass ionomer composition as described herein that includes a first paste including water, a polyacid, and a non acid-reactive filler; and a second paste including water, an acid-reactive filler; and non-aggregated, water-miscible, nano-sized silica particles having at least 25% surface coverage of the particles with a silane; wherein the composition is essentially free of a resin, wherein the device includes a first compartment containing the first paste and a second compartment containing the second paste; combining the first paste and the second paste to form a mixture; and allowing the mixture to cure to form the cured composition.

The curable paste/paste GI compositions disclosed herein can advantageously provide improved storage stability compared to known paste/paste GI compositions, while retaining the mechanical strength (e.g., flexural strength and fracture toughness) typical of cured compositions from known paste/liquid GI compositions due, for example, to low water content.

As used herein, the phrase "substantially crystalline inorganic fibers" refers to inorganic fibers that have minimal amorphous character (i.e., substantially non-amorphous) as evidenced by a sharp x-ray diffraction (XRD) peak. The phrase "substantially crystalline inorganic fibers" is intended to exclude glassy fibers and glass ceramic fibers. In some embodiments, substantially crystalline inorganic fibers have a crystallinity index of at least 0.05, and in certain embodiments a crystallinity index of at least 0.1, as measured by the XRD Crystallinity Index Test Method as described herein. The Crystallinity Index is a parameter used to characterize the level of crystallinity present in a sample of an inorganic fiber. In brief, in the XRD Crystallinity Index Test Method further described herein, tungsten powder is used as internal standard. An internal or mass standard refers to a material incorporated into samples being evaluated to determine crystallinity index, to normalize X-ray intensity values based on amount of material present in sample. Each inorganic fiber sample tested is mixed with tungsten powder in a 4:1 ratio by weight. Each inorganic fiber sample preparation is mixed as an ethanol slurry and then dried, and two sample preparations are made for each inorganic fiber sample tested. Six XRD scans of each sample preparation are then taken. The crystallinity index is the ratio of peak area observed for analyte crystalline phase diffraction peaks within the 14 to 46 degree (2Theta) scattering angle range and the (110) diffraction peak area for the tungsten internal standard.

As used herein, a "dental composition" or a "composition for dental use" or a "composition to be used in the dental field" refers to any composition that can be used in the dental field. In this respect the composition should be not detrimental to the patients' health and thus free of hazardous and toxic components being able to migrate out of the composition. Dental compositions are typically hardenable compositions that can be hardened at ambient conditions, including a temperature range from about 15 to 50° C. or from about 20 to 40° C. within a time frame of about 30 minutes or 20 minutes or 10 minutes. Higher temperatures are not recommended as they might cause pain to the patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is within these ranges.

As used herein, a "polymerizable component" refers to any component that can be cured or solidified, for example, by heating to cause polymerization or chemical crosslinking.

As used herein, the term "resin" refers to a polymerizable component that contains one, two, three, or more polymerizable groups. Exemplary polymerizable groups include, but are not limited to, unsaturated organic groups, such as vinyl groups such as found in a (methyl)acrylate group. A resin can often be cured by radiation induced polymerization or crosslinking, or by using a redox initiator.

As used herein, the term "monomer" refers to any chemical substance that can be characterized by a chemical formula, bearing polymerizable groups (e.g., (meth)acrylate groups) that can be polymerized to oligomers or polymers, thereby increasing the molecular weight. The molecular weight of monomers can typically be calculated from the given chemical formula.

As used herein, "(meth)acryl" is a shorthand term referring to "acryl" and/or "methacryl." For example, a "(meth)acryloxy" group is a shorthand term referring to either an acryloxy group (i.e., $CH_2=CH-C(O)-O-$) and/or a methacryloxy group (i.e., $CH_2=C(CH_3)-C(O)-O-$).

As used herein, the term "initiator" refers to a substance capable of starting or initiating a curing process for resins or monomers, for example, by a redox/auto-cure chemical reaction, by a radiation induced reaction, or by a heat induced reaction.

As used herein, the term "powder" refers to a dry, bulk solid composed of a large number of very fine particles that may flow freely when shaken or tilted.

As used herein, the term "particle" refers to a substance being a solid having a shape that can be geometrically determined. Particles can typically be analyzed with respect to, for example, grain size or diameter.

The mean particle size of a powder can be obtained from various techniques including laser diffraction particle size analysis. The cumulative curve of the grain size distribution can be obtained and defined as the arithmetic average of the measured grain sizes of a certain powder mixture. Respective measurements can be done using available diffraction laser particle size analyzers such as Beckman Coulter LS 13320 Laser Diffraction Particle Size Analyzer or granulometers such as CILAS Laser Diffraction Particle Size Analysis Instrument.

As used herein, the term "dX" (micrometers) with respect to particle size measurements means that X % of the particles in the analyzed volume have a size below the indicated value in micrometers. For example, a particle size value of 100 micrometers (d50) means that within the analyzed volume, 50% of the particles have a size below 100 micrometers.

As used herein, the term "paste" refers to a soft, viscous mass of solids dispersed in a liquid.

As used herein, the term "viscous" refers to a material having a viscosity above about 3 Pa*s (at 23° C.).

As used herein, the term "liquid" refers to any solvent or liquid that is able to at least partially disperse or dissolve a component at ambient conditions (e.g., 23° C.). A liquid typically has a viscosity below about 10 or below about 8 or below about 6 Pa*s.

As used herein, a "glass ionomer cement" or a "GIC" refers to a cement capable of curing or hardening by the reaction between an acid-reactive glass and a polyacid in the presence of water.

As used herein, a "resin modified glass ionomer cement" or "RM-GIC" refers to a GIC additionally containing a resin, an initiator system, and typically 2-hydroxylethyl methacrylate (HEMA).

As used herein, a "conventional glass ionomer cement or restorative" refers to a glass ionomer cement or restorative that is free of a resin, or essentially free of a resin.

As used herein, a composition is "essentially free of" or "substantially free of" a certain component (e.g., a resin), if the composition does not contain said component as an essential feature. Thus, said component is not intentionally added to the composition either as such or in combination with other components or ingredients of other components.

A composition being essentially free of a certain component (e.g., a resin) usually contains the component in an amount of less than about 5 wt.-%, less than about 1 wt.-%, less than about 0.5 wt.-%, or less than about 0.01 wt.-%, with respect to the total weight of the composition or material. The composition may not contain said component at all.

However, sometimes the presence of a small amount of the said component can be unavoidable, for example, due to impurities contained in the raw materials used.

As used herein, an "acid-reactive filler" refers to a filler that can chemically react in the presence of a polyacid leading to a hardening reaction.

As used herein, a "non acid-reactive filler" refers to a filler, that when mixed with a polyacid, (i) does not show a chemical reaction within 6 minutes, or (ii) only shows a reduced (e.g., time-delayed) hardening reaction.

To distinguish an acid-reactive filler from a non acid-reactive filler the following test can or is to be conducted: A composition is prepared by mixing a first part and a second part in a mass ratio of 1 to 3, wherein: the first part contains: poly (acrylic acid-co-maleic acid) (Mw: about 20,000+/−3, 000): 43.6 wt.-%, water: 47.2 wt.-%, tartaric acid: 9.1 wt.-%, and benzoic acid: 0.1 wt.-%; and the second part contains: filler to be analyzed: 100 wt.-%.

The filler is characterized as non acid-reactive, if within 6 minutes after preparing the above composition the shear stress is less than 50,000 Pa determined by conducting an oscillating measurement using a rheometer under the following conditions: using an 8 millimeter plate, 0.75 millimeter gap, at 28° C., frequency: 1.25 Hz, and deformation: 1.75%.

As used herein "nanosilica" is used synonymously with "nano-sized silica particles," and refers to silica particles having an average size of at most 200 nanometers.

As used herein for a spherical particle, "size" refers to the diameter of the particle. As used herein for a non-spherical particle, "size" refers to the longest dimension of the particle.

As used herein, the term "silica sol" refers to a stable dispersion of discrete, amorphous silica particles in a liquid, typically water.

As used herein, the terms "pyrogenic silica" and "fumed silica" are used interchangeably and refer to amorphous silicas formed in the vapor phase. Pyrogenic silica may contain, for example, a few hundred primary particles fused into branched-chain, three-dimensional aggregates. Examples of pyrogenic silica include products available under the trade designations AEROSIL OX-50, AEROSIL-130, AEROSIL-150, and AEROSIL-200 available from DeGussa AG, (Hanau, Germany) and CAB-O-SIL M5 available from Cabot Corp (Tuscola, Ill.).

As used herein, "non-pyrogenic silica" refers to amorphous silica that is not formed in the vapor phase. Examples of non-pyrogenic silicas include precipitated silicas and silica gels.

As used herein, "silane treated" means that the surface of a particle has been modified by application of a silane.

As used herein, "aggregated silica" is descriptive of an association of primary silica particles often bound together by, for example, residual chemical treatment, covalent chemical bonds, or ionic chemical bonds. Although complete breakdown of aggregated silica into smaller entities may be difficult to achieve, limited or incomplete breakdown may be observed under conditions including, for example, shearing forces encountered during dispersion of the aggregated silica in a liquid.

As used herein a "cation reduced aluminosilicate glasses" refers to a glass having a lower content of cations in the surface region of the glass particle compared with the inner region of the glass particle. Such glasses typically react much slower upon contact with a solution of polyacrylic acid in water as compared to typical acid-reactive fillers. Examples of non acid-reactive fillers include quartz glass or strontium oxide based glasses. Further examples are described herein. Cation reduction can be achieved by a surface treatment of the glass particles. Useful surface treatments include, but are not limited to, acid washing (e.g., treatment with a phosphoric acid), treatment with a phosphate, treatment with a chelating agent such as tartaric acid, and treatment with a silane or an acidic or basic silanol solution.

As used herein, the terms "polyacid" and/or "polyalkenoic acid" refer to polymers having a plurality of acidic repeating units (e.g., more than 10 or more than 20 or more than 50). That is, the acidic repeating units are attached to or pending from the backbone of the polymer.

As used herein, the phrase "complexing agent" refers to a low molecular agent capable of forming a complex with metal ions such as, for example, calcium and/or magnesium. An exemplary complexing agent is tartaric acid.

As used herein, the terms "hardenable" and/or "curable" refer to compositions that can be cured or solidified, for example, by conducting a glass ionomer cement reaction without the need for an additional curing system such as chemical cross-linking and/or radiation-induced polymerization or crosslinking.

As used herein, the phrase "ambient conditions" refers to conditions to which paste/paste GI compositions as described herein are typically subjected during storage and handling. Ambient conditions may include, for example, a pressure of about 900 mbar to about 1100 mbar, a temperature of about −10° C. to about 60° C., and/or a relative humidity of about 10% to about 100%. In the laboratory ambient conditions are typically adjusted to about 23° C. and about 1 atmosphere (e.g., 0.95 to 1.05 atmosphere). In the dental and orthodontic field ambient conditions are reasonably understood to include, for example, a pressure of about 950 mbar to about 1050 mbar, a temperature of about 15° C. to about 40° C., and/or a relative humidity of about 20% to about 80%.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one."

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain situations by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Also, as used herein in connection with a measured quantity, the term "approximately" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Many powder/liquid GI compositions are difficult to mix due to high powder/liquid ratios. When such difficulty in mixing is encountered, dentists sometimes lower the powder/liquid ratio below the manufacturer's recommendation to improve mixing properties. Although hand mixing properties may be improved, lowered powder/liquid ratios typically result in decreased mechanical strength of the cured composition.

Disclosed herein are paste/paste GI compositions that can allow for easier hand-mixing, as well as more reproducible and effective dosing of the ingredients. Further, in the paste/paste GI compositions disclosed herein, the second paste includes non-aggregated, water-miscible, nano-sized silica particles having at least 25% surface coverage of the particles with a silane. The pastes including non-aggregated, water-miscible, nano-sized silica particles having at least 25% surface coverage of the particles with a silane can result in the composition remaining sufficiently workable or mixable to form a curable glass ionomer composition after storage at room temperature for at least one month, at least three months, or at least six months.

Known paste/paste GI compositions typically require a higher water content than comparable powder/liquid GI compositions, and the higher water content often results in decreased mechanical strength of the cured composition. However, in the paste/paste GI compositions disclosed herein, in which the second paste includes non-aggregated, water-miscible, nano-sized silica particles having at least 25% surface coverage of the particles with a silane, the mechanical strength of the cured GI composition has been found to be equivalent, and in some cases greater, than that for cured conventional powder/liquid GI compositions. Further, the paste/paste GI compositions disclosed herein, in which the second paste includes non-aggregated, water-miscible, nano-sized silica particles having at least 25% surface coverage of the particles with a silane, can retain the ease of mixing observed with other known paste/paste GI compositions.

Disclosed herein are curable glass ionomer compositions that include a first paste and a second paste. The first paste includes water, a polyacid, and a non acid-reactive filler. The second paste includes water, an acid-reactive filler; and non-aggregated, water-miscible, nano-sized silica particles having at least 25% surface coverage of the particles with a silane. In certain embodiments, the GI composition is essentially free of a resin or free of a resin (e.g., a conventional GI composition). In some embodiments, the water content of the first paste and the second paste of the paste/paste GI composition disclosed herein is less than 20% by weight, based on the total weight of the composition. In some embodiments, the water content of the first paste is less than 20% by weight, based on the total weight of the first paste; and the water content of the second paste is less than 20% by weight, based on the total weight of the second paste.

Polyacids

The first paste of the paste/paste GI compositions disclosed herein includes a polyacid. A wide variety of polyacids can be used in the paste/paste GI compositions disclosed herein. In some embodiments, the polyacid has a molecular weight sufficient to provide good storage, handling, and mixing properties, as well as to yield good material properties in the glass ionomer composition.

In one embodiment, the polyacid can be characterized by at least one or more or all of the following parameters: being a solid (at 23° C.); and molecular weight (Mw) of about 2,000 to about 250,000, or of about 5,000 to about 100,000 (e.g., evaluated against a polyacrylic acid sodium salt standard using gel permeation chromatography).

If the molecular weight of the polyacid is too high, obtaining a workable consistency of the obtained paste when mixing the compositions contained in the GI composition described herein might become difficult. Further, preparation of the compositions might become difficult. In addition, the obtained mixture or composition might become too sticky (e.g., adhere to the dental instrument used for application).

If the molecular weight of the polyacid is too low, the viscosity of the obtained paste might become too low and result in decreased mechanical strength.

Typically, the polyacid is a polymer having a plurality of acidic repeating units.

Useful polyacids for the paste/paste GI compositions disclosed herein are substantially free of polymerizable groups, or free of polymerizable groups.

Useful polyacids need not be entirely water soluble, but typically they are at least sufficiently water-miscible so that they do not undergo substantial sedimentation when combined with other aqueous components.

The polyacid is hardenable in the presence of, for example, an acid-reactive filler and water, but preferably does not contain ethylenically unsaturated groups. That is, the polyacid is a polymer obtained by polymerizing an unsaturated acid. However, due to the production process, a polyacid might still contain unavoidable traces of free monomers (e.g., up to 1 or 0.5 or 0.3 wt.-% with respect to the amount of monomers used). Typically, the unsaturated acid is an oxyacid (i.e., an oxygen containing acid) of carbon, sulfur, phosphorous, or boron. More typically, it is an oxyacid of carbon. Useful polyacids include, for example, polyalkenoic acids such as homopolymers and copolymers of unsaturated mono-, di-, or tricarboxylic acids.

Polyalkenoic acids can be prepared by the homopolymerization and copolymerization of unsaturated aliphatic carboxylic acids, e.g., acrylic acid, methacrylic acid, itaconic acid, maleic acid, glutaconic acid, aconitic acid, citraconic acid, mesaconic acid, fumaric acid, and tiglic acid.

Useful polyacids also include alternating copolymers of maleic acid and ethylene (e.g., in a molar one to one ratio).

Useful polyacids are also described in the following documents: U.S. Pat. No. 4,209,434 (Wilson et al.) and U.S. Pat. No. 4,360,605 (Schmitt et al.).

Useful polyacids are also available, for example, as aqueous solutions in the liquid component of products such as those available under the trade designation KETAC FIL PLUS HANDMIX from 3M ESPE, or under the trade designation FUJI IX GP HANDMIX from G-C Dental Industrial Corp., Tokyo, Japan.

The amount of polyacid used in the paste/paste GI compositions disclosed herein should be sufficient to react with the acid-reactive filler, and to provide an ionomer composition with desirable hardening properties.

In certain embodiments, the polyacid is present in the first paste in an amount of at least 3 wt.-%, at least 5 wt.-%, or at least 10 wt.-%, based on the total weight of the first paste. In certain embodiments, the polyacid is present in the first paste in an amount of at most 70 wt.-%, 60 wt.-%, or 50 wt.-%, based on the total weight of the first paste. In certain embodiments, the polyacid is present in the first paste in an amount of 3 wt.-% to 70 wt.-%; 5 wt.-% to 60 wt.-%, or 10 wt.-% to 50 wt.-%, based on the total weight of the first paste.

If the amount of the polyacid is too high, obtaining a workable consistency of the obtained paste when mixing the compositions contained in the paste/paste GI composition disclosed herein might become difficult. Further, preparation of the compositions might become difficult. In addition, the obtained mixture or composition might become too sticky (e.g., adheres to the dental instrument used for application).

If the amount of the polyacid is too low, obtaining a workable consistency of the obtained paste when mixing the compositions contained in the paste/paste GI composition disclosed herein might become difficult. Further, it will become difficult to achieve the desired mechanical properties.

Non Acid-Reactive Fillers

The first paste of the paste/paste GI compositions disclosed herein includes a non acid-reactive filler. The second paste of the paste/paste GI compositions disclosed herein also includes a non acid-reactive filler that is the same as or different than the non acid-reactive filler in the first paste. The non-acid reactive filler can include, for example, particles and/or fibers (e.g., substantially crystalline inorganic fibers as described herein below).

A non acid-reactive filler is a filler that when combined with a polyacid in the presence of water either (i) does not cure in a glass ionomer cement reaction at all, or (ii) that only shows a delayed curing reaction.

A wide variety of non acid-reactive fillers can be used in the paste/paste GI compositions disclosed herein. In certain embodiments, the non acid-reactive filler is an inorganic filler. In certain embodiments, the non acid-reactive filler is non-toxic and suitable for use in the mouth of a human being. A non acid-reactive filler can be radiopaque or radiolucent. Optionally, the surface of the particles of a non acid-reactive filler can be surface treated (e.g., with silanes).

In certain embodiments, the non acid-reactive filler can include quartz, nitrides, kaolin, borosilicate glass, strontium oxide based glass, barium oxide based glass, silica, alumina, titania, zirconia, or a combination thereof.

In certain embodiments, the non acid-reactive filler can include a metal oxide such as alumina, silica, zirconia, titania, or a combination thereof. In some embodiments the metal oxide can further include modifiers or dopants such as sodium, magnesium, lithium, calcium, strontium, barium, yttrium, ytterbium, lanthanum, zinc, iron, manganese, bismuth oxides, or a combination thereof.

In certain embodiments, the non acid-reactive filler has a mean particle size of 0.005 micrometer to 20 micrometers. For some embodiments, the non acid-reactive filler has a mean particle size of 0.01 micrometer to 10 micrometers. In certain embodiments, the non acid-reactive filler has a d50 of less than 10 micrometers. For embodiments in which both the first paste and the second paste include a non acid-reactive fillers, the mean particle size of the non acid-reactive filler in the second paste can be the same or different than the mean particle size of the non acid-reactive filler in the first paste.

Exemplary non acid-reactive filler are further described, for example, in International Application Publication No. WO 2017/015193 A1 (Jahns et al.).

In certain embodiments, the non acid-reactive filler can be provided as a dispersion or sol of particles in a liquid (e.g., water). If the filler is provided as an aqueous dispersion or sol, the amount of water in the aqueous dispersion or sol has to be taken into account when the amount of water and filler in the composition is calculated or determined.

In certain embodiments, the non acid-reactive filler can include non-aggregated, water-miscible, nano-sized silica particles having at least 25% surface coverage of the particles with a silane, as further discussed herein below.

For the paste/paste GI compositions disclosed herein, the first paste includes at least 10 wt.-% non acid-reactive filler, at least 25 wt.-% non acid-reactive filler, or at least 35 wt.-% non acid-reactive filler, based on the total weight of the first paste. For the paste/paste GI compositions disclosed herein, the first paste includes at most 80 wt.-% non acid-reactive filler, at most 70 wt.-% non acid-reactive filler, or at most 60 wt.-% non acid-reactive filler, based on the total weight of the first paste.

For the paste/paste GI compositions disclosed herein, the second paste includes a non acid-reactive filler, which may include, among other fillers, non-aggregated, water-miscible, nano-sized silica particles having at least 25% surface coverage of the particles with a silane. The second paste includes at least 1 wt.-% non acid-reactive filler, at least 3 wt.-% non acid-reactive filler, or at least 5 wt.-% non acid-reactive filler, based on the total weight of the second paste. For the paste/paste GI compositions disclosed herein, the second paste includes at most 50 wt.-% non acid-reactive filler, at most 40 wt.-% non acid-reactive filler, or at most 30 wt.-% non acid-reactive filler, based on the total weight of the second paste.

Nano-Sized Silica Particles

In the glass ionomer compositions disclosed herein, the second paste includes non-aggregated, water-miscible, nano-sized silica particles having at least 25% surface coverage of the particles with a silane. In some embodiments, the non-aggregated, nano-sized silica particles are substantially free of fumed silica (i.e., pyrogenic silica). However pyrogenic fillers (e.g., fumed silica) can be added as optional additives to the dental compositions.

A wide variety of non-aggregated, nano-sized silica particles can be surface treated as described herein. In some embodiments, the non-aggregated, nano-sized silica particles are available as a silica sol. In certain embodiments, the starting silica sol is NALCO 2329 or LEVASIL 50/50.

Exemplary non-aggregated, nano-sized silica particles include those available from Nalco Chemical Co. (Naperville, Ill.) under the product designation NALCO COLLOIDAL SILICAS (e.g., NALCO products 1040, 1042, 1050, 1060, 2327 and 2329), Nissan Chemical America Company, Houston, Tex. (e.g., SNOWTEX-ZL, -OL, -O, -N, -C, -20L, -40, and -50); Admatechs Co., Ltd., Japan (e.g., SX009-MIE, SX009-MIF, SC1050-MJM, and SC1050-MLV); Grace GmbH & Co. KG, Worms, Germany (e.g., those available under the product designation LUDOX, e.g., P-W50, P-W30, P-X30, P-T40 and P-T40AS); Akzo Nobel Chemicals GmbH, Leverkusen, Germany (e.g., those available under the product designation LEVASIL, e.g., 50/50, 100/45, 200/30%, 200A/30, 200/40, 200A/40, 300/30 and 500/15), and Bayer Material Science AG, Leverkusen, Germany (e.g., those available under the product designation DISPERCOLL S, e.g., 5005, 4510, 4020 and 3030). Further exemplary fillers including non-aggregated, nano-sized silica particles and methods of preparing the fillers are disclosed in, for example, International Publication No. WO 01/30307 (Craig et al.).

For embodiments in which the dental composition further includes pyrogenic fillers (e.g., fumed silica), a wide variety of pyrogenic fillers such as fumed silica can be used. Exemplary fumed silicas include for example, products sold under the trade designations AEROSIL series OX-50, -130, -150, and -200, Aerosil R8200 available from Degussa AG, (Hanau, Germany), CAB-O-SIL M5 available from Cabot Corp (Tuscola, Ill.), and HDK types, e.g. HDK-H 2000, HDK H15; HDK H18, HDK H20 and HDK H30 available from Wacker.

In one embodiment, the non-aggregated, nano-sized silica particles have an average particle size of at most about 200 nanometers, in some embodiments at most about 150 nanometers, and in certain embodiments at most about 120 nanometers. In one embodiment, the non-aggregated, nano-sized silica particles have an average particle size of at least about 20 nanometers, in some embodiments at least about 50 nanometers, and in certain embodiments at least about 70 nanometers. These measurements can be based on a TEM (transmission electron microscopy) method, whereby a population of particles is analyzed to obtain an average particle size.

An exemplary method for measuring the particle diameter can be described is as follows:
Samples approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200Kv. A population size of about 50-100 particles can be measured and an average diameter can be determined.

In one embodiment, the average surface area of the non-aggregated, nano-sized silica particles is at least about 15 m²/g, and in some embodiments at least about 30 m²/g.

In some embodiments, the non-aggregated, nano-sized silica particles used in the dental pastes disclosed in the present application are substantially spherical and substantially non-porous. Although the silica may be essentially pure in certain embodiments, it may contain small amounts of stabilizing ions such as ammonium and alkaline metal ions in other embodiments.

The non-aggregated, nano-sized silica particles can be surface treated with a silane that can provide for water-miscibility of the treated particles. Surface-treating the nano-sized silica particles before loading into the dental material can provide a more stable dispersion in the paste. Preferably, the surface-treatment stabilizes the nano-sized silica particles so that the particles will be well dispersed in the paste and result in a substantially homogeneous composition. Exemplary methods of surface treating drying nano-sized silica particles are described in U.S. Pat. No. 6,899,948 B2 (Zhang et al.) and EP 0368 657 A2 (Okada et al.).

In certain embodiments, the silane is essentially free of unsaturated polymerizable groups.

In certain embodiments, the silane is of the formula: $(R^1O)_3$—Si—$(CH_2)_n$—$(O\text{-}R^2)_x$—$OR^3$, wherein: $R^1$ is a C1-C3 alkyl group; $R^2$ is a C2-C3 alkylene group; $R^3$ is a C1-C10 alkyl group; n=2 to 6; and x=0 to 200. In certain embodiments, $R^2$ represents —$CH_2CH_2$—. In certain embodiments, n=3.

In other certain embodiments, the silane is of the formula: $(R^1O)_3$—Si—$(CH_2)_n$—$(O$—$R^2)_x$—$OR^3$, wherein: $R^1$ is a C1-C3 alkyl group; $R^2$ is a C2-C3 alkylene group; $R^3$ is 2,3-epoxypropyl; n=2 to 6; and x=0 to 200.

Exemplary silanes include, for example, SILQUEST A-1230 available from Momentive Performance Materials (Waterford, N.Y.); 2-[methoxy-(polyethyleneoxy)$_{6\text{-}9}$propyl] trimethoxysilane, 2-[methoxy-(polyethyleneoxy)$_{9\text{-}12}$ propyl]trimethoxysilane, and [3-(2,3-epoxypropoxy)propyl] trimethoxysilane (i.e., 3-glycidoxyproplytrimethoxysilane) available from Gelest (Morrisville, Pa.).

The non-aggregated, water-miscible, nano-sized silica particles have at least 25% surface coverage of the particles with a silane. In some embodiments, the non-aggregated, water-miscible, nano-sized silica particles have at least 50% surface coverage of the particles with a silane. In certain embodiments, the non-aggregated, water-miscible, nano-sized silica particles have at least 75% surface coverage of the particles with a silane. In some certain embodiments, the non-aggregated, water-miscible, nano-sized silica particles have at least 95% surface coverage of the particles with a silane.

The ratio of silane to silica sol for a "100% theoretical coverage" can be calculated using Equation 1 shown below:

$$\frac{\text{g silane}}{\text{g silica sol}} = 6.25 \times 10^{-4}\,\text{mol}/\text{g} \times \frac{20\text{ nm}}{d} \times MW \times SiO2\ w/w \quad (1)$$

Where d is the diameter of the silica particle (nm), MW is the molecular weight of the silane (g/mol), and $SiO_2$ w/w is the silica weight fraction of the silica sol (w/w).

For example, using Levasil 50/50 as the silica sol and 3-glycidoxypropyltrimethoxysilane as the silane, the ratio for "100% theoretical coverage" is calculated as follows:

$$\frac{\text{g silane}}{\text{g Levasil 50/50}} = 6.25 \times 10^{-4}\ \text{mol}/\text{g} \times \frac{20\text{ nm}}{50\text{ nm}} \times$$
$$236.3\ \text{g/mol} \times 0.5$$
$$= .03 \frac{\text{g silane}}{\text{g Levasil 50/50}}$$

In an exemplary method, the calculated amounts of silica sol and silane can be added into a vessel (e.g., a glass vial or glass jar), and the solution can be allowed to react. Although the reaction temperature and time can vary widely as desired, exemplary reaction conditions can be 80-85° C. for 17 hours. Once the reaction is complete, the silane-treated silica sol can be used as is.

For the paste/paste GI compositions disclosed herein, the second paste includes non-aggregated, water-miscible, nano-sized silica particles having at least 25% surface coverage of the particles with a silane. The second paste includes at least 1 wt.-%, at least 3 wt.-%, or at least 5 wt.-% of the non-aggregated, water-miscible, nano-sized silica particles having at least 25% surface coverage of the particles with a silane, based on the total weight of the second paste. For the paste/paste GI compositions disclosed herein, the second paste includes at most 50 wt.-%, at most 40 wt.-%, or at most 30 wt.-% of the non-aggregated, water-miscible, nano-sized silica particles having at least 25% surface coverage of the particles with a silane, based on the total weight of the second paste.

Acid-Reactive Fillers

The second paste of the paste/paste GI compositions disclosed herein includes an acid-reactive filler.

A wide variety of acid-reactive fillers can be used in the paste/paste GI compositions disclosed herein. The acid-reactive filler can undergo a glass-ionomer cement reaction with a polyacid and water.

Useful acid-reactive fillers include, for example, metal oxides, metal hydroxides, hydroxyapatite, acid-reactive glasses, and combinations thereof. In certain embodiments, the acid-reactive fillers include, for example, inorganic fillers selected from the group consisting of basic metal oxides, metal hydroxides, hydroxyapatite, aluminosilicate glasses, fluoroaluminosilicate glasses, glasses having a Si/Al weight percent ratio less than 1.5, and combinations thereof. Useful metal oxides include, for example, calcium hydroxide, magnesium hydroxide, strontium hydroxide and mixtures thereof.

In certain embodiments the acid-reactive filler is a fluoroaluminosilicate ("FAS") glass. FAS glasses typically contains a sufficient amount of elutable cations such that a hardened dental composition can be obtained when the glass is mixed with the other components of the hardenable composition. In some embodiments, the FAS glass also contains a sufficient amount of elutable fluoride ions so that the hardened composition will have cariostatic properties.

FAS glass can be made from a melt containing fluoride, silica, alumina, and other glass-forming ingredients using techniques familiar to those skilled in the FAS glassmaking art. See, for example, U.S. Pat. No. 4,376,835 (Schmitt et al.) and U.S. Pat. No. 5,250,585 (Guggenberger et al.). In some embodiments, FAS glasses can be prepared by fusing mixtures of silica, alumina, cryolite and fluorite. The FAS glass typically is in the form of particles that are sufficiently finely divided so that they can conveniently be mixed with the other cement components and will perform well when the resulting mixture is used in the mouth.

Useful FAS glasses are known in the art and are available from a wide variety of sources, and many are found in currently available glass ionomer cements such as, for example, those available under the trade designations KETAC-MOLAR or KETAC-FIL PLUS from 3M ESPE Dental, and under the trade designation FUJI-IX available from G-C Dental Industrial Corp., Tokyo, Japan.

In certain embodiments, the acid-reactive filler has a mean particle size of 3 micrometers to 10 micrometers. If the mean particle size of the acid-reactive filler is above this range, the consistency of the composition obtained when mixing the compositions contained in the paste/paste GI composition described herein may be less than desired, and the mechanical properties may be less than desired. If the mean particle size of the acid-reactive filler is below this range, the setting time of the paste/paste GI compositions described herein may be faster than desired.

Exemplary acid-reactive fillers are further described, for example, in International Application Publication No. WO 2015/088956 A1 (Peez et al.).

For the paste/paste GI compositions disclosed herein, the second paste includes at least 40 wt.-% acid-reactive filler, at least 50 wt.-% acid-reactive filler, or at least 60 wt.-% acid-reactive filler, based on the total weight of the second paste. For the paste/paste GI compositions disclosed herein, the second paste includes at most 90 wt.-% acid-reactive filler, at most 88 wt.-% acid-reactive filler, or at most 86 wt.-% acid-reactive filler, based on the total weight of the second paste.

If the amount of the acid-reactive filler is too high, the pastes of the paste/paste GI compositions described herein may not be adequately mixed, and obtaining an adequate consistency and acceptable mechanical properties of the resulting composition might become difficult.

If the amount of the acid-reactive filler is too low, a useful paste may not be obtained by mixing the respective pastes of the paste/paste GI compositions described herein. Further, the mechanical strength of the cured composition might decrease.

Substantially Crystalline Inorganic Fibers

In some embodiments of the paste/paste GI compositions disclosed herein, at least one of the first paste and the second paste includes substantially crystalline inorganic fibers.

Substantially crystalline inorganic fibers include inorganic fibers that have minimal amorphous character (i.e., substantially non-amorphous) as evidenced by a sharp x-ray diffraction (XRD) peak. Glassy fibers and glass ceramic fibers are typically not substantially crystalline inorganic fibers. In some embodiments, substantially crystalline inorganic fibers have a crystallinity index of at least 0.05, and in certain embodiments a crystallinity index of at least 0.1, as measured by the XRD Crystallinity Index Test Method as described herein. The Crystallinity Index is a parameter used to characterize the level of crystallinity present in a sample of an inorganic fiber. In brief, in the XRD Crystallinity Index Test Method further described herein, tungsten powder is used as internal standard. An internal or mass standard refers to a material incorporated into samples being evaluated to determine crystallinity index, to normalize X-ray intensity values based on amount of material present in sample. Each inorganic fiber sample tested is mixed with tungsten powder in a 4:1 ratio by weight. Each inorganic fiber sample preparation is mixed as an ethanol slurry and then dried, and two sample preparations are made for each inorganic fiber sample tested. Six XRD scans of each sample preparation are then taken. The crystallinity index is the ratio of peak area observed for analyte crystalline phase diffraction peaks within the 14 to 46 degree (2Theta) scattering angle range and the (110) diffraction peak area for the tungsten internal standard.

A wide variety of substantially crystalline inorganic fibers can be used, including ceramic fibers and/or metal oxide fibers. For embodiments in which the substantially crystalline inorganic fibers include metal oxide fibers, a wide variety of metal oxides can be used. Exemplary metal oxides include, but are not limited to, alumina, silica, zirconia, titania, and combinations thereof. Mixed metal oxides such as aluminosilicates typically contain no more than 20% by weight silicates, based on the total weight of the mixed metal oxide to avoid substantial formation of glassy domains. Optionally, the metal oxide can be modified (e.g., doped) with a component selected from the group consisting of sodium, magnesium, lithium, calcium, strontium, barium, yttrium, ytterbium, lanthanum, zinc, iron, manganese, bismuth oxides, and combinations thereof. For embodiments in which the metal oxide includes a modifier or dopant component, the component is typically present at no more than 10% by weight, based on the total weight of the metal oxide to avoid substantial formation of glassy domains.

In certain embodiments of the paste/paste GI compositions disclosed herein, the substantially crystalline inorganic fibers as contained in the pastes have an average diameter of at least 3 micrometers.

In certain embodiments of the paste/paste GI compositions disclosed herein, the substantially crystalline inorganic fibers as contained in the pastes have an average diameter of at most 25 micrometers, or at most 20 micrometers.

In some embodiments of the paste/paste GI compositions disclosed herein, the substantially crystalline inorganic fibers as contained in the pastes have an average aspect ratio of no more than 100:1, no more than 50:1, no more than 25:1, or no more than 15:1.

In certain embodiments of the paste/paste GI compositions disclosed herein, the substantially crystalline inorganic fibers as contained in the pastes have an average aspect ratio of 10:1 to 50:1, or 15:1 to 25:1. In some certain embodiments of the paste/paste GI compositions disclosed herein, the substantially crystalline inorganic fibers as contained in the pastes have an average aspect ratio of about 10:1.

In certain embodiments of the paste/paste GI compositions disclosed herein, the substantially crystalline inorganic fibers as contained in the pastes have an average length of no more than 1 millimeter, or no more than 0.5 millimeter.

In certain embodiments of the paste/paste GI compositions disclosed herein, the substantially crystalline inorganic fibers as contained in the pastes have an average length of at least 25 micrometers.

In certain embodiments of the paste/paste GI compositions disclosed herein, the first paste includes no more than 65% by weight of the substantially crystalline inorganic fibers, based on the total weight of the first paste.

In certain embodiments of the paste/paste GI compositions disclosed herein, the second paste includes no more than 65% by weight of the substantially crystalline inorganic fibers, based on the total weight of the second paste.

In certain embodiments of the paste/paste GI compositions disclosed herein, the composition includes no more than 40% by weight of the substantially crystalline inorganic fibers, based on the total weight of the composition.

In certain embodiments of the paste/paste GI compositions disclosed herein, the composition includes 10% by weight to 15% by weight of the substantially crystalline inorganic fibers, based on the total weight of the composition.

Water Content

The water in the paste/paste GI compositions disclosed herein can be distilled, de-ionized, or plain tap water. Typically, de-ionized water is used. The amount of water should be sufficient to provide adequate handling and mixing properties and to permit the transport of ions, particularly in the cement reaction.

If the amount of the water is too low, obtaining a workable consistency of the obtained paste might become difficult. If the amount of water is too high, obtaining of a workable consistency of the obtained paste might become difficult, too. Further, it may become difficult to achieve the desired mechanical properties.

For some embodiments of the paste/paste GI compositions disclosed herein, the water content of the first paste and the second paste combined is less than 20% by weight, less than 19% by weight, less than 18% by weight, less than 17% by weight, less than 16% by weight, or less than 15% by weight, based on the total weight of the composition.

In certain embodiments of the paste/paste GI compositions disclosed herein, the water content of the first paste and the second paste combined is at least 10% by weight, and in some embodiments at least 15% by weight, based on the total weight of the composition.

In certain embodiments of the paste/paste GI compositions disclosed herein, the water content of the first paste is less than 20% by weight, less than 19% by weight, less than 18% by weight, less than 17% by weight, less than 16% by weight, or less than 15% by weight, based on the total weight of the first paste.

In certain embodiments of the paste/paste GI compositions disclosed herein, the water content of the second paste is less than 20% by weight, less than 19% by weight, less than 18% by weight, less than 17% by weight, less than 16% by weight, or less than 15% by weight, based on the total weight of the second paste.

Optional Complexing Agent

In certain embodiments, the first paste may optionally include a complexing agent.

For embodiments in which the first paste includes a complexing agent, a wide variety of complexing agents can be used. Useful complexing agent can be characterized by one or more of: being soluble in water (at least 50 g/l water at 23° C.); having a molecular weight of 50 g/mol to 500 g/mol, or having a molecular weight of from 75 g/mol to 300 g/mol.

Exemplary complexing agents include, but are not limited to, tartaric acid, citric acid, ethylene diamine tetra acetic acid (EDTA), salicylic acid, mellitic acid, dihydroxy tartaric acid, nitrilotriacetic acid (NTA), 2,4 and 2,6 dihydroxybenzoic acid, phosphono carboxylic acids, phosphono succinic acid and mixtures thereof. Further examples of complexing agents can be found, for example, U.S. Pat. No. 4,569,954 (Wilson et al.).

For embodiments of the paste/paste GI composition disclosed herein in which the first paste includes a complexing agent, the first paste includes at least 0.1 wt.-% complexing agent, at least 1.0 wt.-% complexing agent, or at least 1.5 wt.-% complexing agent, based on the total weight of the first paste. For the paste/paste GI compositions disclosed herein in which the first paste includes a complexing agent, the first paste includes at most 12 wt.-% complexing agent, at most 10 wt.-% complexing agent, or at most 8 wt.-% complexing agent, based on the total weight of the first paste.

Optional Additives

The paste/paste GI compositions disclosed herein may optionally include various additives known in the art including, but not limited to, flavorants, fluoridating agents, buffering agents, numbing agents, remineralization agents, desensitization agents, colorants, indicator(s), viscosity modifiers, surfactants, stabilizers, preservative agents (e.g., benzoic acid), or combinations thereof. The presence of a colorant can aid in detecting that the aqueous composition has coated all the desired intraoral surfaces. The intensity of a colorant can also aid in detecting the uniformity of the coating on the intraoral surfaces.

For embodiments of the paste/paste GI composition disclosed herein in which an additive is present in the first paste, the first paste includes at least 0.01 wt.-% additive, at least 0.05 wt.-% additive, or at least 0.1 wt.-% additive, based on the total weight of the first paste. For the paste/paste GI compositions disclosed herein in which an additive is present in the first paste, the first paste includes at most 5 wt.-% additive, at most 3 wt.-% additive, or at most 1 wt.-% additive, based on the total weight of the first paste.

For embodiments of the paste/paste GI composition disclosed herein in which an additive is present in the second paste, the second paste includes at least 0.01 wt.-% additive, at least 0.05 wt.-% additive, or at least 0.1 wt.-% additive, based on the total weight of the second paste. For the paste/paste GI compositions disclosed herein in which an additive is present in the second paste, the second paste includes at most 5 wt.-% additive, at most 3 wt.-% additive, or at most 1 wt.-% additive, based on the total weight of the second paste.

Typically neither the first paste nor the second paste of the paste/paste GI composition disclosed herein contains any of the following components, alone or in combination: a)

HEMA in an amount above 1 wt.-% or above 0.5 wt.-%; b) resin(s) in an amount above 1 wt.-% or above 0.5 wt.-%; c) initiator component(s) suitable to cure resin(s) or monomer (s) in an amount above 1 wt.-% or above 0.5 wt.-%; d) inhibitor(s) like methoxyphenol or 3,5-Di-tert-butyl-4-hydroxytoluol in an amount above 1 wt.-% or above 0.5 wt.-%; e) desiccant(s) like zeolithe(s) in an amount above 1 wt.-% or above 0.5 wt.-%. Thus, the composition obtained when mixing the pastes of the paste/paste GI composition is not a resin-modified glass ionomer cement (RM-GIC), and thus does not contain a curing system based on polymerization.

Accordingly, in certain embodiments, the paste/paste GI compositions disclosed herein do not contain a redox-initiator system or a thermally induced initiator system or a radiation induced initiator system.

First Paste and Second Paste

The first paste can typically be characterized by having a pH less than 7.

The second paste can typically be characterized by having a pH greater than 7.

Optionally, the first paste and/or the second paste can each independently further include a solvent. In some embodiments, adding a solvent or co-solvent can help to adjust the viscosity and consistency of the composition.

Examples of useful solvents include alcohols (e.g., methanol, ethanol, and propanol), polyalcohols/polyols (e.g., ethylene glycol and glycerol), and combinations thereof.

Devices

The first paste and the second paste of the paste/paste GI compositions described herein can be provided to the practitioner in various embodiments.

In one embodiment, the pastes may be contained in separate sealable vessels (e.g., made out of plastic or glass). For use, the practitioner may take adequate portions of the paste components from the vessels and mix the portions by hand on a mixing plate.

In some embodiments, the pastes are contained in separate compartments of a storage device. The storage device typically includes two compartments for storing the respective pastes, each compartment being equipped with a nozzle for delivering the respective paste. Once delivered in adequate portions, the pastes can then be mixed by hand on a mixing plate.

In certain embodiments, the storage device has an interface for receiving a static mixing tip. The mixing tip is used for mixing the respective pastes. Static mixing tips are available from, for example, SulzerMixpac Company. Useful storage devices include cartridges, syringes, and tubes.

The storage device typically includes two housings or compartments having a front end with a nozzle and a rear end and at least one piston movable in the housing or compartment.

Useful cartridges are described, for example, in U.S. Patent Application Pub. No. 2007/0090079 A1 (Keller et al.) and U.S. Pat. No. 5,918,772 (Keller et al.). Useful cartridges are available from, for example, SulzerMixpac AG (Switzerland). Useful static mixing tips are described, for example, in U.S. Patent Application Pub. No. 2006/0187752 A1 (Keller et al.) and in U.S. Pat. No. 5,944,419 (Streiff). Useful mixing tips are available from, for example, Sulzer-Mixpac AG (Switzerland).

Other useful storage devices are described, for example, in WO 2010/123800 (3M), WO 2005/016783 (3M), WO 2007/104037 (3M), WO 2009/061884 (3M).

Alternatively, paste/paste GI compositions described herein can be provided in two individual syringes and the individual pastes can be mixed by hand prior to use.

In certain embodiments the paste/paste GI composition disclosed herein can be provided as a kit that includes the first paste, the second paste, and instructions describing one or more methods (as disclosed herein) for mixing the first paste and the second paste to form a cured composition.

In one embodiment, the present disclosure provides a device for storing a curable glass ionomer composition as described herein that includes a first paste including water, a polyacid, and a non acid-reactive filler; and a second paste including water, an acid-reactive filler; and non-aggregated, water-miscible, nano-sized silica particles having at least 25% surface coverage of the particles with a silane; wherein the composition is essentially free of a resin. The device includes: a first compartment containing the first paste; and a second compartment containing the second paste. In some embodiments, both the first compartment and the second compartment each independently includes a nozzle or an interface for receiving an entrance orifice of a static mixing tip.

In some embodiments, the mixing ratio of first paste and the second paste is 1:3 to 2:1 with respect to volume, and in certain embodiments, 1:2 to 2:1 with respect to volume.

In other embodiments, the mixing ratio of first paste and the second paste is 1:6 to 1:1 with respect to weight, and in certain embodiments 1:4 to 1:1 with respect to weight.

The composition obtained or obtainable when mixing the respective pastes is in particular useful as or for producing a dental cement, dental filling material, dental core build up material or as dental root channel filling material.

Methods

A practitioner can use the paste/paste GI compositions disclosed herein in a wide variety of methods to prepare a cured composition.

In one embodiment, the method includes: providing a curable glass ionomer composition as described herein that includes a first paste including water, a polyacid, and a non acid-reactive filler; and a second paste including: water, an acid-reactive filler; and non-aggregated, water-miscible, nano-sized silica particles having at least 25% surface coverage of the particles with a silane; wherein the composition is essentially free of a resin; combining the first paste and the second paste to form a mixture (e.g., a hardenable composition); and allowing the mixture to cure to form the cured composition.

In another embodiment, the method includes: providing a device for storing a curable glass ionomer composition as described herein that includes a first paste including water, a polyacid, and a non acid-reactive filler; and a second paste including water, an acid-reactive filler; and non-aggregated, water-miscible, nano-sized silica particles having at least 25% surface coverage of the particles with a silane; wherein the composition is essentially free of a resin, wherein the device includes: a first compartment containing the first paste; and a second compartment containing the second paste; combining the first paste and the second paste to form a mixture (e.g., a hardenable composition); and allowing the mixture to cure to form the cured composition.

In certain embodiments, the mixture (e.g., hardenable composition) is applied to the surface of hard dental tissue, and the mixture (e.g., hardenable composition) is allowed to cure and form a cured composition on the surface of the hard dental tissue.

According to one embodiment the cement composition obtained or obtainable by mixing the two pastes of the GI composition disclosed herein can fulfil at least one, more than one, or all of the following parameters before or during hardening: setting time within about 5 minutes, 4 minutes, or 3 minutes determined according to EN-ISO 9917-1:2007; working time within about 4 minutes, 3 minutes, 2 minutes, or 1 minute determined according to EN-ISO 9917-1:2007; and being storage stable. If desired, the setting time and curing behavior can be determined as described in more detail in the Example section herein.

In certain embodiments, the mixture (e.g., hardenable composition) formed from mixing the first paste and the second paste of the paste/paste GI composition disclosed herein has a sufficient working time to allow the practitioner not only to adequately mix the composition, but also to apply the composition to the surface of, for example, a crown, bridge, root canal or prepared tooth. Further, the mixture (e.g., hardenable composition) has a conveniently short setting time that can save time for the practitioner and enhance convenience for the patient.

According to another embodiment, the mixture (e.g., hardenable composition) formed from mixing the first paste and the second paste of the paste/paste GI composition disclosed herein can fulfil one, more than one, or all of the following parameters after hardening: flexural strength above about 20 MPa, or above about 25 MPa, determined according to EN-ISO 9917-2:2010 with the proviso that for covering the composition a glass slab is used instead of a foil; compressive strength above about 100 MPa, above about 120 MPa, or above about 150 MPa, determined according to EN-ISO 9917-1/2007, with the proviso that for covering the composition a glass slab is used instead of a foil. If desired, these parameters can be determined as described in the Example section herein.

Compared to commercially available state of the art glass ionomer cements, paste/paste GI compositions disclosed herein can be readily mixed and can provide adequate mechanical properties such as flexural strength and fracture toughness, without affecting other important parameters such as setting time. Typically, the paste/paste GI compositions disclosed herein can provide adequate adhesion to dental surfaces such as enamel and dentin.

ILLUSTRATIVE EMBODIMENTS OF THE PRESENT DISCLOSURE

Various embodiments are disclosed that can provide curable glass ionomer compositions and methods of using same.

Embodiment 1A is a curable glass ionomer composition comprising: a first paste comprising: water, a polyacid, and a non acid-reactive filler; and a second paste comprising: water, an acid-reactive filler; and non-aggregated, water-miscible, nano-sized silica particles having at least 25% surface coverage of the particles with a silane; wherein the composition is essentially free of a resin.

Embodiment 2A is the curable glass ionomer composition of Embodiment 1A, wherein the composition is free of a resin.

Embodiment 3A is the composition according to embodiment 1A or 2A wherein the silane is essentially free of unsaturated polymerizable groups.

Embodiment 4A is the composition according to any one of embodiments 1A to 3A wherein the silane is of the formula: $(R^1O)_3$—Si—$(CH_2)_n$—$(O$—$R^2)_x$—$OR^3$, wherein: $R^1$ is a C1-C3 alkyl group; $R^2$ is a C2-C3 alkylene group; $R^3$ is a C1-C10 alkyl group; n=2 to 6; and x=0 to 200.

Embodiment 5A is the composition according to any one of embodiments 1A to 3A wherein the silane is of the formula: $(R^1O)_3$—Si—$(CH_2)_n$—$(O$—$R^2)_x$—$OR^3$, wherein: $R^1$ is a C1-C3 alkyl group; $R^2$ is a C2-C3 alkylene group; $R^3$ is 2,3-epoxypropyl; n=2 to 6; and x=0 to 200.

Embodiment 6A is the composition according to embodiment 4A or 5A wherein $R^2$ represents —$CH_2CH_2$—.

Embodiment 7A is the composition according to any one of embodiments 4A to 6A wherein n=3.

Embodiment 8A is the composition according to any one of embodiments 1A to 7A wherein the non-aggregated, water-miscible, nano-sized silica particles have at least 50% surface coverage of the particles with a silane.

Embodiment 9A is the composition according to any one of embodiments 1A to 8A wherein the non-aggregated, water-miscible, nano-sized silica particles have at least 75% surface coverage of the particles with a silane.

Embodiment 10A is the composition according to any one of embodiments 1A to 9A wherein the non-aggregated, water-miscible, nano-sized silica particles have at least 95% surface coverage of the particles with a silane.

Embodiment 11A is the composition according to any one of embodiments 1A to 10A wherein the non-aggregated, water-miscible, nano-sized silica particles are substantially free of fumed silica.

Embodiment 12A is the composition according to any one of embodiments 1A to 11A wherein at least one of the first paste and the second paste further comprises pyrogenic silica particles.

Embodiment 13A is the composition according to any one of embodiments 1A to 12A wherein the water content of the first paste and the second paste combined is less than 20% by weight, based on the total weight of the composition.

Embodiment 14A is the composition according to any one of embodiments 1A to 13A wherein the water content of the first paste is less than 20% by weight, based on the total weight of the first paste; and the water content of the second paste is less than 20% by weight, based on the total weight of the second paste.

Embodiment 15A is the composition according to any one of embodiments 1A to 14A wherein the water content of the first paste and the second paste combined is less than 19% by weight, based on the total weight of the composition.

Embodiment 16A is the composition according to any one of embodiments 1A to 15A wherein the water content of the first paste and the second paste combined is less than 18% by weight, based on the total weight of the composition.

Embodiment 17A is the composition according to any one of embodiments 1A to 16A wherein the water content of the first paste and the second paste combined is less than 17% by weight, based on the total weight of the composition.

Embodiment 18A is the composition according to any one of embodiments 1A to 17A wherein the water content of the first paste and the second paste combined is less than 16% by weight, based on the total weight of the composition.

Embodiment 19A is the composition according to any one of embodiments 1A to 18A wherein the water content of the first paste and the second paste combined is less than 15% by weight, based on the total weight of the composition.

Embodiment 20A is the composition according to any one of embodiments 1A to 19A wherein the water content of the first paste and the second paste combined is 10% by weight to 15% by weight, based on the total weight of the composition.

Embodiment 21A is the composition according to any one of embodiments 1A to 20A wherein the non acid-reactive filler comprises particles and/or fibers.

Embodiment 22A is the composition according to any one of embodiments 1A to 21A wherein the non acid-reactive filler is selected from the group consisting of quartz, nitrides, kaolin, borosilicate glass, strontium oxide based glass, barium oxide based glass, silica, alumina, titania, zirconia, and combinations thereof.

Embodiment 23A is the composition according to any one of embodiments 1A to 22A wherein the non acid-reactive filler comprises a metal oxide selected from the group consisting of alumina, silica, zirconia, titania, and combinations thereof.

Embodiment 24A is the composition according to any one of embodiments 1A to 23A wherein the non acid-reactive filler has a mean particle size of 0.005 micrometer to 10 micrometers.

Embodiment 25A is the composition according to any one of embodiments 1A to 24A wherein the non acid-reactive filler comprises substantially crystalline inorganic fibers.

Embodiment 26A is the composition according to embodiment 25A wherein the substantially crystalline inorganic fibers comprise ceramics and/or metal oxides.

Embodiment 27A is the composition according to embodiment 25A or 26A wherein the substantially crystalline inorganic fibers comprise a metal oxide selected from the group consisting of alumina, silica, zirconia, titania, and combinations thereof.

Embodiment 28A is the composition according to embodiment 27A wherein the metal oxide is modified with a component selected from the group consisting of sodium, magnesium, lithium, calcium, strontium, barium, yttrium, ytterbium, zinc, iron, manganese, bismuth oxides, and combinations thereof.

Embodiment 29A is the composition according to any one of embodiments 25A to 28A wherein the substantially crystalline inorganic fibers as contained in the pastes have an average diameter of at least 3 micrometers.

Embodiment 30A is the composition according to any one of embodiments 25A to 29A wherein the substantially crystalline inorganic fibers as contained in the pastes have an average diameter of at most 25 micrometers.

Embodiment 31A is the composition according to any one of embodiments 25A to 30A wherein the substantially crystalline inorganic fibers as contained in the pastes have an average diameter of at most 20 micrometers.

Embodiment 32A is the composition according to any one of embodiments 25A to 31A wherein the substantially crystalline inorganic fibers as contained in the pastes have an average aspect ratio of about 10:1.

Embodiment 33A is the composition according to any one of embodiments 25A to 32A wherein the substantially crystalline inorganic fibers as contained in the pastes have an average length of no more than 1 millimeter.

Embodiment 34A is the composition according to any one of embodiments 25A to 33A wherein the substantially crystalline inorganic fibers as contained in the pastes have an average length of no more than 0.5 millimeter.

Embodiment 35A is the composition according to any one of embodiments 25A to 34A wherein the substantially crystalline inorganic fibers as contained in the pastes have an average length of at least 25 micrometers.

Embodiment 36A is the composition according to any one of embodiments 25A to 35A wherein the substantially crystalline inorganic fibers have a crystallinity index of at least 0.05 as measured by the XRD Crystallinity Index Test Method.

Embodiment 37A is the composition according to any one of embodiments 25A to 35A wherein the substantially crystalline inorganic fibers have a crystallinity index of at least 0.1 as measured by the XRD Crystallinity Index Test Method.

Embodiment 38A is the composition according to any one of embodiments 25A to 37A wherein the first paste comprises no more than 65% by weight of the substantially crystalline inorganic fibers, based on the total weight of the first paste.

Embodiment 39A is the composition according to any one of embodiments 25A to 38A wherein the second paste comprises no more than 65% by weight of the substantially crystalline inorganic fibers, based on the total weight of the second paste.

Embodiment 40A is the composition according to any one of embodiments 25A to 39A wherein the composition comprises no more than 40% by weight of the substantially crystalline inorganic fibers, based on the total weight of the composition.

Embodiment 41A is the composition according to any one of embodiments 25A to 40A wherein the composition comprises 10% by weight to 15% by weight of the substantially crystalline inorganic fibers, based on the total weight of the composition.

Embodiment 42A is the composition according to any one of embodiments 1A to 41A wherein the acid-reactive filler comprises an inorganic filler selected from the group consisting of basic metal oxides, metal hydroxides, hydroxyapatite, aluminosilicate glasses, fluoroaluminosilicate glasses, glasses having a Si/Al weight percent ratio less than 1.5, and combinations thereof.

Embodiment 43A is the composition according to any one of embodiments 1A to 42A wherein the acid-reactive filler has a mean particle size of 3 micrometers to 10 micrometers.

Embodiment 44A is the composition according to any one of embodiments 1A to 43A wherein the first paste further comprises a complexing agent.

Embodiment 45A is the composition according to any one of embodiments 1A to 44A wherein the composition remains sufficiently workable or mixable to form a curable glass ionomer composition after storage at room temperature for at least one month.

Embodiment 46A is the composition according to any one of embodiments 1A to 45A wherein the composition remains sufficiently workable or mixable to form a curable glass ionomer composition after storage at room temperature for at least three months.

Embodiment 47A is the composition according to any one of embodiments 1A to 46A wherein the composition remains sufficiently workable or mixable to form a curable glass ionomer composition after storage at room temperature for at least six months.

Embodiment 1B is a method of preparing a cured composition comprising: providing a curable glass ionomer composition according to any one of embodiments 1A to 47A; combining the first paste and the second paste to form a mixture; and allowing the mixture to cure to form the cured composition.

Embodiment 1C is a device for storing the composition according to any one of embodiments 1A to 47A comprising: a first compartment containing the first paste; and a second compartment containing the second paste.

Embodiment 2C is the device of embodiment 1C, wherein both the first compartment and the second compartment each independently comprises a nozzle or an interface for receiving an entrance orifice of a static mixing tip.

Embodiment 1D is a method of preparing a cured composition comprising: providing a device according to embodiment 1C or 2C; combining the first paste and the second paste to form a mixture; and allowing the mixture to cure to form the cured composition.

Objects and advantages of this disclosure are further illustrated by the following non-limiting examples, but the particular materials and amounts thereof recited in these examples, as well as other conditions and details, should not be construed to unduly limit this disclosure.

EXAMPLES

The following examples are given to illustrate, but not limit, the scope of this invention. As used herein, all parts and percentages are by weight and all water was deionized, unless otherwise specified. Unless otherwise specified, materials can be obtained from Sigma-Aldrich Corp. (St. Louis, Mo.). All commercial materials were used as obtained from the vendor. Ammonium fluoride was obtained from Alfa Aesar (Tewksbury, Mass.). Tartaric acid was obtained from Fisher Scientific (Waltham, Mass.), 3-Phosphonopropionic acid was obtained from Alfa Aesar (Tewksbury, Mass.).

XRD Crystallinity Index Test Method

The Crystallinity Index is a parameter used to characterize the level of crystallinity present in a sample of an inorganic fiber. In brief, in the XRD Crystallinity Index Test Method used herein, tungsten powder is used as internal standard. An internal or mass standard refers to a material incorporated into samples being evaluated to determine crystallinity index, to normalize X-ray intensity values based on amount of material present in sample. Each inorganic fiber sample tested is mixed with tungsten powder in a 4:1 ratio by weight. Each inorganic fiber sample preparation is mixed as an ethanol slurry and then dried, and two sample preparations are made for each inorganic fiber sample tested. Six XRD scans of each sample preparation are then taken. The crystallinity index is the ratio of peak area observed for analyte crystalline phase diffraction peaks within the 14 to 46 degree (2Theta) scattering angle range and the (110) diffraction peak area for the tungsten internal standard. The following procedure was used to measure the XRD Crystallinity Index for the tested substantially crystalline inorganic fibers.

Particle size of the phase standard was reduced by ball milling and/or hand grinding in a boron carbide mortar and pestle to pass 325 mesh sieve. Individual mixtures were prepared consisting of 0.400 grams of each sample and 0.100 grams of tungsten internal standard (i.e., tungsten metal powder, <3 micron, available from General Electric, Lot U-1.35-8808D). Mixtures were blended under ethanol in a mortar and pestle and allowed to dry under flowing nitrogen. The dried mixtures were removed from the mortar and pestle by spatula and fine brush and finally transferred to individual sample containers.

Portions of each sample were prepared as ethanol slurries on zero background specimen holders composed of silicon. Multiple X-ray diffraction scans were obtained from each sample by use of a Bragg-Bretano theta-theta diffractometer (Empyrean, constructed by PANalytical, Almelo, The Netherlands) employing copper $K_\alpha$ radiation, variable entrance slit, fixed exit slit, and Pixcel detector registry of the scattered radiation. Scans were conducted from 14 to 46 degrees (2θ) employing a 0.026 degree step size and 10 second dwell time. The X-ray generator was operated at a setting of 40 kV and 40 mA and fixed incident beam slits were used.

Peak areas for the observed diffraction maxima due to crystalline phases within the sample and tungsten mass standard were measured by profile fitting observed diffraction peaks within the 14-46 degree (2θ) scattering angle range. The X-ray scattering of internal mass standard was evaluated by measurement of cubic tungsten using the (11 0) peak area. When necessary, the scattering due to amorphous phases was accounted for by including a sufficient number of suitably broad scattering peaks during the profile fitting procedure. A Pearson VII peak shape model and linear background model were employed in all cases. The profile fitting was accomplished by use of the capabilities of the JADE (Version 9, Materials Data Inc. Livermore, Calif.) diffraction software suite.

The peak areas for maxima produced by crystalline phases present in the sample were summed to produce a total sample crystalline phase scattered intensity value [(Total Crystalline Area)$_{sample}$] for each sample. Any broad peaks used to account for amorphous phases during profile fitting were not included in crystallinity index calculations. These total sample crystalline phase scattered intensity values were divided by respective cubic tungsten (11 0) peak area to produce the crystallinity index [$X_c$] for each sample:

$X_c$=[(Total Crystalline Area)$_{sample}$]/[(Tungsten Area) sample]

The mean $X_c$ value was calculated from individual $X_c$ values:

$X_{c(mean)}$=[$\Sigma X_{c(i)}$]/$N_{sample}$, where $N_{sample}$=number of sample scans. Multiple XRD runs of a sample were reported.

The Crystallinity Index results measured according to this procedure are reported in Table 1.

TABLE 1

Measured Crystallinity Indices

| | Crystallinity Index (std. dev.) | |
|---|---|---|
| Sample | Sample Preparation 1 | Sample Preparation 2 |
| Nextel 312 | 0 | 0 |
| Nextel 720 | 1.82 (0.71) | 1.51 (0.40) |
| Zirconia | 3.87 (0.98) | 4.08 (2.58) |
| Corundum (approximately 100% crystalline) | 0.94 (0.12) | 0.79 (0.07) |
| Nextel 610 1500d | 0.82 (0.03) | 0.70 (0.03) |

No detectable diffraction peaks were observed for the Nextel 312 samples.

Materials

"NALCO 2329" refers to an aqueous colloidal silica sol containing 40 wt. % $SiO_2$, sodium counter ion (approximately 0.25% $Na_2O$), pH=8.4 at 25° C., 75 nm particle size, available from Ecolab (Naperville, Ill.);

"LEVASIL 50/50" refers to an aqueous colloidal silica sol containing 50 wt. % $SiO_2$, base-stabilized colloidal silica sol, pH=9-10, 50 nm particle size, available from Akzo Nobel (Bohus, Sweden);

"PA 1" refers to a water soluble polyacid copolymer of acrylic acid and maleic acid (1:1 copolymer) with a MW of approximately 20,000 (KETAC-FIL PLUS (3M ESPE Dental Products);

"FAS 1" refers to an acid-reactive fluoroaluminosilicate glass powder, mean particle size: 4.8 μm (d10 of 1.6 μm; d508.0 μm; d90 of 30 μm) with the following elemental composition: Si: 10-15 wt. %; Al: 10-15 wt. %; Sr: 23-26.5 wt. %; Na: 2.0-4.0 wt. %; F: 11.0-14.5 wt. %; P: 2-3.5 wt. %; La: 4.5-7 wt. %; 0: 26-30 wt. % (based on X-ray fluorescence analysis). The acid reactive glass powder is prepared by melting a glass frit, subsequently crushing and grinding the frit to particle size of 4.8 rpm, followed by washing with 1M hydrochloric acid for 1 hour, filtering, drying and tempering at 200-300° C. for 12 hours.

"FAS 2" refers to an acid-reactive fluoroaluminosilicate glass powder, mean particle size: 4.8 μm with the following elemental composition: Si: 7.5-12.5 wt. %; Al: 7.5-12.5 wt. %; La: 15.0-20.0 wt. %; Ca: 7.5-12.5 wt. %; Na: 1.0-3.0 wt. %; P: 0.5-3.0 wt. %; F: 12.0-17.0 wt. %; O: 30.0-35.0 wt. % (based on X-ray fluorescence analysis). The acid reactive glass powder is prepared by melting a glass frit, subsequently crushing and grinding the frit to particle size of 4.8 m, followed by washing with 1M hydrochloric acid for 1 hour, filtering, drying and tempering at 200-300° C. for 12 hours.

"NEXTEL 720" refers to aluminosilica ceramic fibers having α-$Al_2O_3$ and Mullite crystal phases (85 wt. % $Al_2O_3$, 15 wt. % $SiO_2$), 10-12 μm diameter, available from 3M which were further chopped to uniform lengths of 200 μm. "S/T NEXTEL 720" refers to NEXTEL 720 which was surface-treated as follows. To a stirring mixture of the chopped fiber in water (5 times the weight of the chopped fiber) was added 3-phosphonopropionic acid (2 wt. %, based on the weight of the fiber). The mixture was heated to 100° C. and stirred for a minimum of 2 hours. The fibers were allowed to settle approximately 30 minutes), and the supernatant liquid decanted. The fibers were washed with excess water (twice) and the damp fibers were dried at 85° C. for approximately 2 hours to provide the NEXTEL 720 chopped fibers.

"Silquest A-1230" refers to a polyalkyleneoxidealkoxysilane with a molecular weight of approximately 600 g/mol, obtained from Momentive Performance Materials (Waterford, N.Y.).

"Methoxypropyltrimethoxysilane" refers to a hydrophilic silane with a molecular weight of 194 g/mol, obtained from Gelest, Inc (Morrisville, Pa.).

"Carboxyethylsilanetriol" refers to a hydrophilic silane with a molecular weight of 196 g/mol, obtained from Gelest, Inc (Morrisville, Pa.).

"Acetoxyethyltrimethoxysilane" refers to a hydrophilic silane with a molecular weight of 208 g/mol, obtained from Gelest, Inc (Morrisville, Pa.).

"Aerosil 300 Pharma" refers to a fumed silica with a surface area of about 300 m²/g, obtained from Evonik Industries (Essen, Germany).

Methods

Preparation of Silane-Treated Silica Sols

Silane treatments were performed by reacting a solution of silica sol (such as Levasil 50/50 or Nalco 2329) with a silane (such as Silquest A-1230). The ratio of silane to silica sol for a "100% theoretical coverage" was calculated by using Equation 1 shown below:

$$\frac{\text{g silane}}{\text{g silica sol}} = 6.25 \times 10^{-4} \, \text{mol}/g \times \frac{20 \text{ nm}}{d} \times MW \times SiO2 \, w/w \quad (1)$$

Where d is the diameter of the silica particle (nm), MW is the molecular weight of the silane (g/mol), and SiO2 w/w is the silica weight fraction of the silica sol (w/w). For example, if Levasil 50/50 was the silica sol being used, and 3-glycidoxypropyltrimethoxysilane was the silane, the ratio for "100% theoretical coverage" would have been calculated as follows:

$$\frac{\text{g silane}}{\text{g Levasil 50/50}} = 6.25 \times 10^{-4} \, \text{mol}/g \times \frac{20 \text{ nm}}{50 \text{ nm}} \times$$

$$236.3 \text{ g/mol} \times 0.5$$

$$= .03 \frac{\text{g silane}}{\text{g Levasil 50/50}}$$

Once the correct amounts of silica sol and silane were added into a vessel (usually a glass vial or glass jar), the solution would be allowed to react. The most common reaction conditions were 80-85 C for 17 hours; however, the exact temperature and time is not overly significant. Once the reaction time was complete, the silane-treatment was done, and the sol was ready to use.

Preparation of Glass Ionomer Pastes Generally

All pastes were created by using a high shear speed mixer (FlackTek Inc. Speed Mixer, DAC 150 FVZ & 150.1 FVZ). Base pastes were created by adding all ingredients, and mixing at 2000-2500 RPM for 1 minute. This tended to be enough for a complete mix of the base paste. Acid pastes were created by addition of water, tartaric acid, and PA 1. The solution was then speed mixed at 3500 RPM for 1 minute, to break up the solids. S/T Nextel 720 fiber was then added, and the paste was speed mixed at 3500 RPM for 1 minute. This was then followed by a series of hand-spatulating followed by speed mixing at 3500 RPM for 1 minute until a homogenous paste was achieved.

Flexural Strength

Glass ionomer test specimens were prepared by mixing the two parts at the ratios indicated in the tables below, and placing the mixed material into a 2 millimeter×2 millimeter× 25 millimeter PEEK (polyether ether ketone) mold with polyester film on both sides. Polycarbonate slides were placed outside of both pieces of polyester film. The mold was then clamped with a power hand clamp and put into a temperature and humidity controlled chamber for about 1 hour at 37° C. and 95% relative humidity. The sample was then removed from mold, placed into deionized water, and put into a 37° C. oven for about 24 hours. Samples were then polished using 600 grit sandpaper on a Buehler Ecomet 4 Variable Speed Grinder-Polisher to smooth edges, and accurately measure width and length. Flexural strength was measured on an Instron tester (Instron 5944, Instron Corp., Canton, Mass., USA) according to ANSI/ADA (American National Standard/American Dental Association) specification No. 27 (1993) at a crosshead speed of 0.75 millimeer/minute.

Storage Stability

Pastes of the example compositions were placed into BD Slip Tip syringes (5 or 10 mL) and dispensed into heat-sealable aluminum pouches. Pouches were heat-sealed to be air-tight and water-tight, labelled, and massed. 10-15 pouches of paste were made for each formulation. Pouches were placed into a plastic zipper-closing bag, and placed into a 25° C., 50% Relative Humidity environment. Samples were observed for aging at various time points. Samples were massed before observing to verify that no water loss had taken place. At end of each respective storage time period, examples were opened and evaluated with a probe for softness and workability as an acceptable paste. Sample results were grouped into three rating categories: (1) "++"

indicated the samples exhibited no noticeable change over the storage conditions, they were still a soft workable, mixable paste and considered acceptable; (2) "+" indicated the examples exhibited some amount of change, they were not as soft but were still a workable, mixable paste and marginally acceptable; (3) "−" indicated the samples exhibited definite unacceptable change, they were a hardened paste and not workable. Stability results are shown in Tables 30-32.

Formulations

Silane-Treated Silica Sols

The silane-treated silica sols which were used in experimentation can be seen below in Tables 2-5:

TABLE 2

A-1230 Silane-Treated Silica Sol Formulations

| % Theoretical Coverage | Silica Sol Name | % Silica Sol | % A-1230 Silane |
|---|---|---|---|
| 100% | Levasil 50/50 | 93.0% | 7.0% |
| 100% | Nalco 2329 | 96.5% | 3.5% |
| 75% | Levasil 50/50 | 94.7% | 5.3% |
| 75% | Nalco 2329 | 97.4% | 2.6% |
| 50% | Levasil 50/50 | 96.4% | 3.6% |
| 50% | Nalco 2329 | 98.2% | 1.8% |
| 25% | Levasil 50/50 | 98.2% | 1.8% |
| 25% | Nalco 2329 | 99.1% | 0.9% |
| 10% | Levasil 50/50 | 99.2% | 0.8% |

TABLE 3

Methoxypropyltrimethoxysilane-Treated Silica Sol Formulations

| % Theoretical Coverage | Silica Sol Name | % Silica Sol | % Methoxypropyltrimethoxysilane |
|---|---|---|---|
| 100% | Levasil 50/50 | 97.6% | 2.4% |
| 50% | Levasil 50/50 | 98.7% | 1.3% |
| 25% | Levasil 50/50 | 99.3% | 0.7% |

TABLE 4

Carboxyethylsilanetriol-Treated Silica Sol Formulations

| % Theoretical Coverage | Silica Sol Name | % Silica Sol | % Carboxyethylsilanetriol |
|---|---|---|---|
| 100% | Levasil 50/50 | 97.9% | 2.1% |
| 50% | Levasil 50/50 | 98.9% | 1.1% |
| 25% | Levasil 50/50 | 99.4% | 0.6% |

TABLE 5

Acetoxyethyltrimethoxysilane-Treated Silica Sol Formulations

| % Theoretical Coverage | Silica Sol Name | % Silica Sol | % Acetoxyethyltrimethoxysilane |
|---|---|---|---|
| 100% | Levasil 50/50 | 97.5% | 2.5% |

*This sol gelled upon reaction and had a mashed potatoes-like consistency

Paste Formulations

The base pastes which were created for storage stability testing can be seen below in Tables 6-23:

TABLE 6

Paste Formulation of Comparative Example 1 for Storage Stability Testing

Comparative Example 1

| Material | Weight % |
|---|---|
| FAS 1 | 80.8 |
| Levasil 50/50 | 19.2 |

TABLE 7

Paste Formulation of Example 1 for Storage Stability Testing

Example 1

| Material | Weight % |
|---|---|
| FAS 1 | 80.0 |
| 25% A-1230 Coverage Levasil 50/50 | 19.0 |
| Aerosil 300 Pharma | 1.0 |

TABLE 8

Paste Formulation of Example 2 for Storage Stability Testing

Example 2

| Material | Weight % |
|---|---|
| FAS 1 | 80.0 |
| 50% A-1230 Coverage Levasil 50/50 | 19.0 |
| Aerosil 300 Pharma | 1.0 |

TABLE 9

Paste Formulation of Example 3 for Storage Stability Testing

Example 3

| Material | Weight % |
|---|---|
| FAS 1 | 82.2 |
| 50% A-1230 Coverage Nalco 2329 | 16.9 |
| Aerosil 300 Pharma | 1.0 |

TABLE 10

Paste Formulation of Example 4 for Storage Stability Testing

Example 4

| Material | Weight % |
|---|---|
| FAS 1 | 78.8 |
| 100% A-1230 Coverage Levasil 50/50 | 19.2 |
| Aerosil 300 Pharma | 2.0 |

TABLE 11

Paste Formulation of Example 5 for Storage Stability Testing

Example 5

| Material | Weight % |
|---|---|
| FAS 1 | 81.2 |
| 100% A-1230 Coverage Nalco 2329 | 16.9 |
| Aerosil 300 Pharma | 2.0 |

TABLE 12

Paste Formulation of Comparative Example 2 for Storage Stability Testing
Comparative Example 2

| Material | Weight % |
|---|---|
| FAS 2 | 73.0 |
| Levasil 50/50 | 26.0 |
| Aerosil 300 Pharma | 1.0 |

TABLE 13

Paste Formulation of Comparative Example 3 for Storage Stability Testing
Comparative Example 3

| Material | Weight % |
|---|---|
| FAS 2 | 73.0 |
| 10% A-1230 Coverage Levasil 50/50 | 26.0 |
| Aerosil 300 Pharma | 1.0 |

TABLE 14

Paste Formulation of Example 6 for Storage Stability Testing
Example 6

| Material | Weight % |
|---|---|
| FAS 2 | 73.0 |
| 25% A-1230 Coverage Levasil 50/50 | 26.0 |
| Aerosil 300 Pharma | 1.0 |

TABLE 15

Paste Formulation of Example 7 for Storage Stability Testing
Example 7

| Material | Weight % |
|---|---|
| FAS 2 | 73.0 |
| 50% A-1230 Coverage Levasil 50/50 | 26.0 |
| Aerosil 300 Pharma | 1.0 |

TABLE 16

Paste Formulation of Example 8 for Storage Stability Testing
Example 8

| Material | Weight % |
|---|---|
| FAS 2 | 73.0 |
| 100% A-1230 Coverage Levasil 50/50 | 26.0 |
| Aerosil 300 Pharma | 1.0 |

TABLE 17

Paste Formulation of Example 9 for Storage Stability Testing
Example 9

| Material | Weight % |
|---|---|
| FAS 2 | 73.0 |
| 25% Methoxypropyltrimethoxysilane Coverage Levasil 50/50 | 26.0 |
| Aerosil 300 Pharma | 1.0 |

TABLE 18

Paste Formulation of Example 10 for Storage Stability Testing
Example 10

| Material | Weight % |
|---|---|
| FAS 2 | 73.0 |
| 50% Methoxypropyltrimethoxysilane Coverage Levasil 50/50 | 26.0 |
| Aerosil 300 Pharma | 1.0 |

TABLE 19

Paste Formulation of Example 11 for Storage Stability Testing
Example 11

| Material | Weight % |
|---|---|
| FAS 2 | 73.0 |
| 100% Methoxypropyltrimethoxysilane Coverage Levasil 50/50 | 26.0 |
| Aerosil 300 Pharma | 1.0 |

TABLE 20

Paste Formulation of Comparative Example 4 for Storage Stability Testing
Comparative Example 4

| Material | Weight % |
|---|---|
| FAS 2 | 73.0 |
| 25% Carboxyethylsilanetriol Coverage Levasil 50/50 | 26.0 |
| Aerosil 300 Pharma | 1.0 |

TABLE 21

Paste Formulation of Comparative Example 5 for Storage Stability Testing
Comparative Example 5

| Material | Weight % |
|---|---|
| FAS 2 | 73.0 |
| 50% Carboxyethylsilanetriol Coverage Levasil 50/50 | 26.0 |
| Aerosil 300 Pharma | 1.0 |

TABLE 22

Paste Formulation of Comparative Example 6 for Storage Stability Testing
Comparative Example 6

| Material | Weight % |
|---|---|
| FAS 2 | 73.0 |
| 100% Carboxyethylsilanetriol Coverage Levasil 50/50 | 26.0 |
| Aerosil 300 Pharma | 1.0 |

TABLE 23

Paste Formulation of Comparative Example 7 for Storage Stability Testing
Comparative Example 7

| Material | Weight % |
|---|---|
| FAS 2 | 73.0 |
| 100% Acetoxyethyltrimethoxysilane Coverage Levasil | 26.0 |

TABLE 23-continued

Paste Formulation of Comparative Example 7 for Storage Stability Testing

Comparative Example 7

| Material | Weight % |
|---|---|
| 50/50 | |
| Aerosil 300 Pharma | 1.0 |

*This formulation did not make an acceptable paste

The formulations which were used to test flexural strength are shown below in Tables 24-29:

TABLE 24

Paste Formulations of Comparative Example 8 for Flexural Strength Testing Comparative Example 8 (1:0.9 weight ratio of acid paste:base paste)

| Material | Acid Paste (wt %) | Base Paste (wt %) | Overall (wt %) |
|---|---|---|---|
| Water | 9.0% | — | 4.7% |
| Tartaric Acid | 3.0% | — | 1.6% |
| PA | 26.0% | — | 13.7% |
| Nextel 720 | — | 10.0% | 4.7% |
| S/T Nextel 720 | 56.0% | — | 29.5% |
| FAS 2 | — | 66.0% | 31.3% |
| Levasil 50/50 | 6.0% | 24.0% | 14.5% |

TABLE 25

Paste Formulations of Example 12 for Flexural Strength Testing Example 12 (1:0.9 weight ratio of acid paste:base paste)

| Material | Acid Paste (wt %) | Base Paste (wt %) | Overall (wt %) |
|---|---|---|---|
| Water | 9.0% | — | 4.7% |
| Tartaric Acid | 3.0% | — | 1.6% |
| PA | 26.0% | — | 13.7% |
| Nextel 720 | — | 10.0% | 4.7% |
| S/T Nextel 720 | 56.0% | — | 29.5% |
| FAS 2 | — | 66.0% | 31.3% |
| Levasil 50/50 | 6.0% | — | 3.2% |
| 25% A-1230 Coverage Levasil 50/50 | | 24.0% | 11.4% |

TABLE 26

Paste Formulations of Example 13 for Flexural Strength Testing Example 13 (1:0.9 weight ratio of acid paste:base paste)

| Material | Acid Paste (wt %) | Base Paste (wt %) | Overall (wt %) |
|---|---|---|---|
| Water | 9.0% | — | 4.7% |
| Tartaric Acid | 3.0% | — | 1.6% |
| PA | 26.0% | — | 13.7% |
| Nextel 720 | — | 10.0% | 4.7% |
| S/T Nextel 720 | 56.0% | — | 29.5% |
| FAS 2 | — | 66.0% | 31.3% |
| Levasil 50/50 | 6.0% | — | 3.2% |
| 50% A-1230 Coverage Levasil 50/50 | | 24.0% | 11.4% |

TABLE 27

Paste Formulations of Example 14 for Flexural Strength Testing Example 14 (1:0.9 weight ratio of acid paste:base paste)

| Material | Acid Paste (wt %) | Base Paste (wt %) | Overall (wt %) |
|---|---|---|---|
| Water | 9.0% | — | 4.7% |
| Tartaric Acid | 3.0% | — | 1.6% |
| PA | 26.0% | — | 13.7% |
| Nextel 720 | — | 10.4% | 4.9% |
| S/T Nextel 720 | 56.0% | — | 29.5% |
| FAS 2 | — | 68.8% | 32.6% |
| Levasil 50/50 | 6.0% | — | 3.2% |
| 50% A-1230 Coverage Nalco 2329 | | 20.8% | 9.9% |

TABLE 28

Paste Formulations of Example 15 for Flexural Strength Testing Example 15 (1:0.9 weight ratio of acid paste:base paste)

| Material | Acid Paste (wt %) | Base Paste (wt %) | Overall (wt %) |
|---|---|---|---|
| Water | 9.0% | — | 4.7% |
| Tartaric Acid | 3.0% | — | 1.6% |
| PA | 26.0% | — | 13.7% |
| Nextel 720 | — | 10.0% | 4.7% |
| S/T Nextel 720 | 56.0% | — | 29.5% |
| FAS 2 | — | 66.0% | 31.3% |
| Levasil 50/50 | 6.0% | — | 3.2% |
| 100% A-1230 Coverage Levasil 50/50 | | 24.0% | 11.4% |

TABLE 29

Paste Formulations of Example 16 for Flexural Strength Testing Example 16 (1:0.9 weight ratio of acid paste:base paste)

| Material | Acid Paste (wt %) | Base Paste (wt %) | Overall (wt %) |
|---|---|---|---|
| Water | 9.0% | — | 4.7% |
| Tartaric Acid | 3.0% | — | 1.6% |
| PA | 26.0% | — | 13.7% |
| Nextel 720 | — | 10.4% | 4.9% |
| S/T Nextel 720 | 56.0% | — | 29.5% |
| FAS 2 | — | 68.8% | 32.6% |
| Levasil 50/50 | 6.0% | — | 3.2% |
| 100% A-1230 Coverage Nalco 2329 | | 20.8% | 9.9% |

Physical Properties Measurement

Stability was measured as described herein for exemplary examples and comparative examples, and the results are shown in Tables 30-32:

TABLE 30

Aging Results of Base Pastes with A-1230 Silane

| Example Number | 2 Weeks | 3 Weeks | 1 Month | 2 Month | 3 Month | 6 Month |
|---|---|---|---|---|---|---|
| Comp. Example 1 | N/A | ++ | ++ | + | + | − |
| Example 1 | N/A | ++ | ++ | ++ | ++ | ++ |
| Example 2 | N/A | ++ | ++ | ++ | ++ | ++ |
| Example 3 | N/A | ++ | ++ | ++ | ++ | ++ |
| Example 4 | N/A | ++ | ++ | ++ | ++ | ++ |
| Example 5 | N/A | ++ | ++ | ++ | ++ | ++ |
| Comp. Example 2 | + | + | − | − | − | − |
| Comp. Example 3 | ++ | + | + | + | + | − |
| Example 6 | ++ | ++ | ++ | ++ | ++ | + |
| Example 7 | ++ | ++ | ++ | ++ | ++ | ++ |
| Example 8 | ++ | ++ | ++ | ++ | ++ | ++ |

In the above table sample results were grouped into three rating categories: (1) "++" indicated the samples exhibited no noticeable change over the storage conditions, they were still a soft workable, mixable paste and considered acceptable; (2) "+" indicated the examples exhibited some amount of change, they were not as soft but were still a workable, mixable paste and marginally acceptable; (3) "−" indicated the samples exhibited definite unacceptable change, they were a hardened paste and not workable.

TABLE 31

Aging Results of Base Pastes with Methoxypropyltrimethoxysilane

| Example Number | 2 Weeks | 3 Weeks | 1 Month | 2 Month | 3 Month |
|---|---|---|---|---|---|
| Example 9 | ++ | ++ | ++ | ++ | ++ |
| Example 10 | ++ | ++ | ++ | ++ | ++ |
| Example 11 | ++ | ++ | ++ | ++ | ++ |

It can be seen that all Examples with methoxypropyltrimethoxysilane did not show signs of aging.

TABLE 32

Aging Results of Base Pastes with Carboxyethylsilanetriol

| Example Number | 2 Weeks | 1 Month | 2 Month | 3 Month |
|---|---|---|---|---|
| Comp. Example 4 | ++ | ++ | + | − |
| Comp. Example 5 | ++ | ++ | + | − |
| Comp. Example 6 | ++ | ++ | ++ | + |

Flexural strengths were measured as described herein for exemplary examples and comparative examples, and the results are shown in Table 33:

TABLE 33

Flexural Strength Analysis of Varying Coverages of Silane-Treated Silica Sols

| Material ID | % A-1230 Coverage/ Silica Sol | Mean (MPa) | Standard Deviation (MPa) | Sample Size (n) |
|---|---|---|---|---|
| Comparative Example 8 | 0%/ Levasil | 55.15 | 6.35 | 5 |
| Example 12 | 25%/ Levasil | 51.45 | 4.20 | 4 |
| Example 13 | 50%/ Levasil | 48.61 | 5.74 | 5 |
| Example 14 | 50%/ Nalco | 53.12 | 8.32 | 5 |
| Example 15 | 100%/ Levasil | 43.41 | 3.12 | 4 |
| Example 16 | 100%/ Nalco | 47.11 | 5.62 | 5 |

It can be seen that while there might be a very slight trend of lower flexural strength with higher theoretical coverage, there is not a statistical significance in flexural strength based on silane-treatment of the silica sol.

Example 17

Example 17 was prepared with the following amounts. Levasil 50/50 from Akzo Nobel was first epoxy silanized according to the procedure described in U.S. Pat. No. 6,899,948 B2 (Zhang et al.), section "Filler C Nano-sized Silica." The silane was 3-Glycidyloxypropyl trimethoxysilane. An amount of 15.2% epoxy silanized Levasil 50/50 (containing 50% water and 50% silanized particles) was added to an amount of 83.1% Ketac Fil Plus ionomer glass powder (KETAC Fil Plus Glass Ionomer Filling Material, available from 3M Company, Seefeld Germany), 1.6% OX-50 fumed silica and 0.1% benzoic acid.

All cited references, patents, or patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A curable glass ionomer composition comprising:
   a first paste comprising:
      water,
      a polyacid, and
      a non acid-reactive filler; and
   a second paste comprising:
      water,
      an acid-reactive filler; and non-aggregated, water-miscible, nano-sized silica particles having at least 25% surface coverage of the particles with a silane;

wherein the composition is essentially free of a resin.

2. The composition of claim 1, or wherein the silane is essentially free of unsaturated polymerizable groups.

3. The composition of claim 1, wherein the silane is represented by the formula:

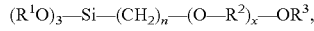

$(R^1O)_3-Si-(CH_2)_n-(O-R^2)_x-OR^3$, wherein:
R$^1$ is a C1-C3 alkyl group;
R$^2$ is a C2-C3 alkylene group;
R$^3$ is a C1-C10 alkyl group or 2,3-epoxypropyl;
n=2 to 6; and
x=0 to 200.

4. The composition of claim 3, or wherein R$^2$ represents —CH$_2$CH$_2$—.

5. The composition of claim 3, wherein n=3.

6. The composition of claim 1, wherein the non-aggregated, water-miscible, nano-sized silica particles are substantially free of fumed silica.

7. The composition of claim 1, wherein at least one of the first paste and the second paste further comprises pyrogenic silica particles.

8. The composition of claim 1, wherein the water content of the first paste and the second paste combined is less than 20% by weight, based on the total weight of the composition.

9. The composition of claim 1, wherein the non acid-reactive filler comprises particles and/or fibers.

10. The composition of claim 1, wherein the non acid-reactive filler is selected from the group consisting of quartz, nitrides, kaolin, borosilicate glass, strontium oxide based glass, barium oxide based glass, silica, alumina, titania, zirconia, and combinations thereof.

11. The composition of claim 1, wherein the non acid-reactive filler comprises substantially crystalline inorganic fibers.

12. The composition of claim 11, wherein the substantially crystalline inorganic fibers comprise ceramics and/or metal oxides.

13. The composition of claim 11, wherein the substantially crystalline inorganic fibers have a crystallinity index of at least 0.05 as measured by the XRD Crystallinity Index Test Method.

14. The composition of claim 1, wherein the acid-reactive filler comprises an inorganic filler selected from the group consisting of basic metal oxides, metal hydroxides, hydroxyapatite, aluminosilicate glasses, fluoroaluminosilicate glasses, glasses having a Si/Al weight percent ratio less than 1.5, and combinations thereof.

15. The composition of claim 1, wherein the acid-reactive filler has a mean particle size of 3 micrometers to 10 micrometers.

16. The composition of claim 1, wherein the first paste further comprises a complexing agent.

17. The composition of claim 1, wherein the composition remains sufficiently workable or mixable to form a curable glass ionomer composition after storage at room temperature for at least one month.

18. The composition of claim 1, wherein the composition remains sufficiently workable or mixable to form a curable glass ionomer composition after storage at room temperature for at least three months.

19. A method of preparing a cured composition comprising:
providing a curable glass ionomer composition of claim 1;
combining the first paste and the second paste to form a mixture; and
allowing the mixture to cure to form the cured composition.

20. A device for storing a composition of claim 1, the device comprising:
a first compartment containing the first paste; and
a second compartment containing the second paste.

* * * * *